(12) United States Patent
Dhawan et al.

(10) Patent No.: US 12,716,028 B2
(45) Date of Patent: Aug. 25, 2026

(54) SUCCINIC ANHYDRIDE-DERIVED POLYESTERS AS CORROSION INHIBITORS

(71) Applicant: Ecolab USA Inc., St. Paul, MN (US)

(72) Inventors: Ashish Dhawan, Aurora, IL (US); Jeremy Moloney, Katy, TX (US); Carter M. Silvernail, Lakeville, MN (US)

(73) Assignee: Ecolab USA Inc., St. Paul, MN (US)

( * ) Notice: Subject to any disclaimer, the term of this patent is extended or adjusted under 35 U.S.C. 154(b) by 1029 days.

(21) Appl. No.: 17/893,974

(22) Filed: Aug. 23, 2022

(65) Prior Publication Data

US 2023/0096673 A1 Mar. 30, 2023

Related U.S. Application Data

(60) Provisional application No. 63/236,571, filed on Aug. 24, 2021.

(51) Int. Cl.

| | |
|---|---|
| ***C09K 15/20*** | (2006.01) |
| ***C07C 219/06*** | (2006.01) |
| ***C10G 75/02*** | (2006.01) |
| ***C23F 11/14*** | (2006.01) |

(52) U.S. Cl.

CPC ............ *C09K 15/20* (2013.01); *C07C 219/06* (2013.01); *C10G 75/02* (2013.01); *C23F 11/141* (2013.01); *C10G 2300/80* (2013.01)

(58) Field of Classification Search

CPC .................................................... C07C 219/06

See application file for complete search history.

(56) References Cited

U.S. PATENT DOCUMENTS

| | | | |
|---|---|---|---|
| 3,522,093 | A | 7/1970 | Woolman |
| 4,024,050 | A | 5/1977 | Shell et al. |
| 4,253,876 | A | 3/1981 | Godar et al. |
| 4,767,551 | A | 8/1988 | Hunt et al. |
| 4,851,524 | A | 7/1989 | Brois et al. |
| 5,176,848 | A | 1/1993 | Kang et al. |
| 5,178,786 | A | 1/1993 | Jahnke et al. |
| 5,308,521 | A | 5/1994 | Pavilon et al. |
| 5,352,377 | A | 10/1994 | Blain et al. |
| 5,556,575 | A | 9/1996 | Babaian-Kibala et al. |
| 5,620,948 | A | 4/1997 | Tipton |
| 6,001,156 | A | 12/1999 | Riggs, Jr. |
| 6,228,253 | B1 | 5/2001 | Gandman |
| 6,444,018 | B1 | 9/2002 | King et al. |
| 6,844,299 | B2 | 1/2005 | Bessonette et al. |
| 6,919,421 | B2 | 7/2005 | Swift |
| 7,311,144 | B2 | 12/2007 | Conrad |
| 10,131,859 | B2 | 11/2018 | Wolf et al. |
| 2007/0245620 | A1 | 10/2007 | Malfar et al. |
| 2019/0062187 | A1 | 2/2019 | Dhawan et al. |

FOREIGN PATENT DOCUMENTS

| | | | |
|---|---|---|---|
| EP | 0414398 | A1 | 2/1991 |
| EP | 1151994 | A1 | 11/2001 |
| RU | 2502748 | C1 | 12/2013 |
| WO | 2017182160 | A1 | 10/2017 |

*Primary Examiner* — Peter F Godenschwager

(74) *Attorney, Agent, or Firm* — Kagan Binder, PLLC

(57) ABSTRACT

Disclosed are succinic anhydride-derived polyester compounds used in compositions and methods for inhibiting corrosion.

19 Claims, No Drawings

SUCCINIC ANHYDRIDE-DERIVED POLYESTERS AS CORROSION INHIBITORS

CROSS REFERENCE TO RELATED APPLICATIONS

This application claims the benefit of U.S. Provisional Patent Application Ser. No. 63/236,571, filed Aug. 24, 2021, the disclosure of which is incorporated in its entirety herein by reference.

BACKGROUND

Corrosion of metal surfaces continues to be a problem in industrial water systems including the oil and gas industry. Such systems can include "corrodents" such as salts, other dissolved solids, liquids, gases or combinations thereof that cause, accelerate, or promote corrosion of metal containments that contact the corrodents. The corrodents can cause severe corrosion as evidenced by surface pitting, embrittlement, and general loss of metal. Corrosion problems are even more troublesome in deep-sea operations where replacement of corroded equipment is difficult and costly. As a result, almost all operators in the oil and gas industry employ corrosion inhibitors to reduce corrosion in metal containments, which contact liquids containing corrodents.

A variety of metal corrosion inhibiting formulations that have been developed. However, these options are not without their problems. Therefore, there continues to be a need for corrosion inhibiting compositions and methods that are effective and minimize operating costs.

SUMMARY

Described herein are compositions and methods for inhibiting corrosion in fluid sources comprising corrodents.

In one aspect is a composition comprising succinic anhydride-derived polyester compounds to inhibit corrosion, the succinic anhydride-derived polyester compounds comprising a polyamine and an alkyl or alkenyl succinic anhydride (ASA) and having the general formula I:

(Formula I)

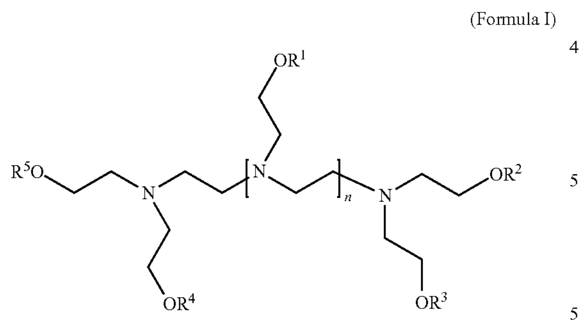

Wherein n is 0-20; and

Wherein $R^1$, $R^2$, $R^3$, $R^4$, and $R^5$ are each individually selected from —H, a ring opened ASA, or cyclic adduct with ASA, wherein at least one of $R^1$, $R^2$, $R^3$, $R^4$, and $R^5$ is an ASA or cyclic adduct with ASA or combination thereof.

In another aspect of the application is a method of inhibiting corrosion comprising introducing into a process equipment or a fluid in contact with the process equipment a composition comprising a succinic anhydride-derived polyester compounds, the succinic anhydride-derived polyester compounds comprising a polyamine and an alkyl or alkenyl succinic anhydride and having the general formula I:

(Formula I)

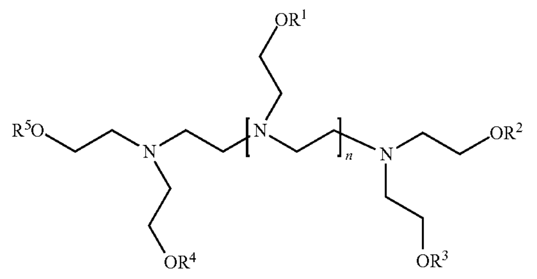

Wherein n is 0-20; and

Wherein $R^1$, $R^2$, $R^3$, $R^4$, and $R^5$ are each individually selected from —H, a ring opened ASA, or cyclic adduct with ASA, wherein at least one of $R^1$, $R^2$, $R^3$, $R^4$, and $R^5$ is an ASA or cyclic adduct with ASA or combination thereof.

In still another aspect is a treated metal containment comprising a metal containment comprising a metal surface; and the fluid source comprising the succinic acid-derived polyesters having the general Formula I, wherein at least a portion of the metal surface is contacted by the fluid source.

DETAILED DESCRIPTION

Although the present disclosure provides references to various embodiments, persons skilled in the art will recognize that changes may be made in form and detail without departing from the spirit and scope of the application. Reference to various embodiments does not limit the scope of the claims attached hereto. Additionally, any examples set forth in this specification are not intended to be limiting and merely set forth some of the many possible embodiments for the appended claims.

Unless otherwise defined, all technical and scientific terms used herein have the same meaning as commonly understood by one of ordinary skill in the art. In case of conflict, the present document, including definitions, will control. Preferred methods and materials are described below, although methods and materials similar or equivalent to those described herein can be used in practice or testing of the present application. All publications, patent applications, patents and other references mentioned herein are incorporated by reference in their entirety.

Compounds described herein can comprise one or more asymmetric centers, and thus can exist in various isomeric forms, e.g., enantiomers and/or diastereomers. For example, the compounds described herein can be in the form of an individual enantiomer, diastereomer or geometric isomer, or can be in the form of a mixture of stereoisomers, including racemic mixtures and mixtures enriched in one or more stereoisomer. Isomers can be isolated from mixtures by methods known to those skilled in the art, including chiral high pressure liquid chromatography (HPLC) and the formation and crystallization of chiral salts; or preferred isomers can be prepared by asymmetric syntheses. See, for example, Jacques et al., *Enantiomers, Racemates and Resolutions* (Wiley Interscience, New York, 1981); Wilen et al., *Tetrahedron* 33:2725 (1977); Eliel, E. L. *Stereochemistry of Carbon Compounds* (McGraw-Hill, N Y, 1962); and Wilen, S. H. *Tables of Resolving Agents and Optical Resolutions* p. 268 (E. L. Eliel, Ed., Univ. of Notre Dame Press, Notre Dame, Ind. 1972). The invention additionally encompasses compounds as individual isomers substantially free of other isomers, and alternatively, as mixtures of various isomers.

As used herein, the term "aliphatic" or "aliphatic group" refers to a straight-chain or branched hydrocarbon chain that is completely saturated or that contains one or more units of unsaturation, or a monocyclic hydrocarbon or bicyclic hydrocarbon that is completely saturated or that contains one or more units of unsaturation, but which is not aromatic.

As used herein, the term "alkyl group" as described herein alone or as part of another group is an optionally substituted linear saturated monovalent hydrocarbon substituent containing from one to sixty carbon atoms in the main chain or an optionally substituted branched saturated monovalent hydrocarbon substituent containing three to sixty carbon atoms. Examples of unsubstituted alkyl groups include methyl, ethyl, n-propyl, i-propyl, n-butyl, butyl, s-butyl, t-butyl, n-pentyl, i-pentyl, s-pentyl, t-pentyl, and the like.

As used herein, the term "alkenyl" refers to an unsaturated hydrocarbon that contains at least one carbon-carbon double bound.

The term "alkoxy" as used herein or alone or as part of another group is an —OR group, wherein the R group is a substituted or unsubstituted alkyl group as defined herein.

The terms "c" or "ar" as used herein alone or as part of another group (e.g., aralkyl) denote optionally substituted homocyclic aromatic groups, or monocyclic or bicyclic groups containing from 6 to 12 carbons in the ring portion, such as phenyl, biphenyl, naphthyl, substituted phenyl, substituted biphenyl or substituted naphthyl. Phenyl and substituted phenyl are the more preferred aryl. The term "aryl" also includes heteroaryl.

As used herein, the term "corrodents," are materials that cause, initiate, catalyze, accelerate, induce, or otherwise promote the corrosion of metals.

As used herein, the term "corrosion inhibitor" means a compound or mixture that prevents, retards, mitigates, reduces, controls and/or delays corrosion.

As used herein, the term "inhibits," "inhibiting," or grammatical equivalents thereof when used in the context of corrosion inhibition refers to preventing, retarding, mitigating, reducing, controlling and/or delaying corrosion.

As used herein, the term "injectate" means water plus any solids or liquids dispersed therein that is injected into a subterranean formation for the purpose of inducing hydrocarbon recovery therefrom. Injectates optionally include salts, polymers, surfactants, scale inhibitors, stabilizers, metal chelating agents, corrosion inhibitors, paraffin inhibitors, and other additives as determined by the operator in a subterranean hydrocarbon recovery process.

As used herein, the term "passivation" means the prevention of a reaction between two materials when used together by coating at least one of the two materials to such an extent that they become substantially less reactive relative to each other.

As used herein, the term "produced water" means water that flows back from a subterranean reservoir and is collected during a hydrocarbon recovery process including, but not limited to hydraulic fracturing and tertiary oil recovery. Produced water includes residual hydrocarbon products entrained therein and one or more of injectate, connate (native water present in the subterranean formation along with the hydrocarbon), brackish water, and sea water. Produced water ranges in temperature from about −30° C. to about 200° C., depending on the subterranean reservoir and the terranean environment and infrastructure proximal to the subterranean reservoir.

As used herein, the term "process equipment" means equipment used to refine, store, transport, fractionate, or otherwise process a material including but not limited to heaters, heat exchangers, tubes, pipes, heat transfer vessels, process vessels, tanks, compressors, fans, impellers, pumps, valves, inter-coolers, sensors, and the like, that are associated with a process and which may be subject to corrosion. This term also includes sets of components which are in communication with each other.

As used herein, the terms "comprise(s)," "include(s)," "having," "has," "can," "contain(s)," and variants thereof are intended to be open-ended transitional phrases, terms, or words that do not preclude the possibility of additional acts or structures. The singular forms "a," "and" and "the" include plural references unless the context clearly dictates otherwise. The present disclosure also contemplates other embodiments "comprising," "consisting of" and "consisting essentially of," the embodiments or elements presented herein, whether explicitly set forth or not.

As used herein, the term "optional" or "optionally" means that the subsequently described event or circumstance may, but need not occur, and that the description includes instances where the event or circumstance occurs and instances in which it does not.

As used herein, the term "about" modifying, for example, the quantity of an ingredient in a composition, concentration, volume, process temperature, process time, yield, flow rate, pressure, and like values, and ranges thereof, employed in describing the embodiments of the disclosure, refers to variation in the numerical quantity that can occur, for example, through typical measuring and handling procedures used for making compounds, compositions, concentrates or use formulations; through inadvertent error in these procedures; through differences in the manufacture, source, or purity of starting materials or ingredients used to carry out the methods, and like proximate considerations. The term "about" also encompasses amounts that differ due to aging of a formulation with a particular initial concentration or mixture, and amounts that differ due to mixing or processing a formulation with a particular initial concentration or mixture. Where modified by the term "about" the claims appended hereto include equivalents to these quantities. Further, where "about" is employed to describe a range of values, for example "about 1 to 5" the recitation means "1 to 5" and "about 1 to about 5" and "1 to about 5" and "about 1 to 5" unless specifically limited by context.

As used herein, the term "substantially" means "consisting essentially of" and includes "consisting of," and these terms are construed as in U.S. patent law. For example, a solution that is "substantially free" of a specified compound or material may be free of that compound or material, or may have a minor amount of that compound or material present, such as through unintended contamination, side reactions, or incomplete purification. A "minor amount" may be a trace, an unmeasurable amount, an amount that does not interfere with a value or property, or some other amount as provided in context. A composition that has "substantially only" a provided list of components may consist of only those components, or have a trace amount of some other component present, or have one or more additional components that do not materially affect the properties of the composition. Additionally, "substantially" modifying, for example, the type or quantity of an ingredient in a composition, a property, a measurable quantity, a method, a value, or a range, employed in describing the embodiments of the disclosure, refers to a variation that does not affect the overall recited composition, property, quantity, method, value, or range thereof in a manner that negates an intended composition, property, quantity, method, value, or range. Where modified by the term "substantially" the claims appended hereto include equivalents according to this definition.

As used herein, any recited ranges of values contemplate all values within the range and are to be construed as support for claims reciting any sub-ranges having endpoints which are real number values within the recited range. By way of example, a disclosure in this specification of a range from 1 to 5 shall be considered to support claims to any of the following ranges: 1-5; 1-4; 1-3; 1-2; 2-5; 2-4; 2-3; 3-5; 3-4; 4-5 and any values there between.

Described herein are compositions and methods directed to an alkyl or alkenyl succinic anhydride (ASA)-derived polyesters. In some embodiments, the ASA-derived polyesters are used to inhibit corrosion of metal containments that contact fluids containing corrodents. In some embodiments, the ASA-derived polyesters are formed by reacting a polyamine compound with an alkyl or alkenyl succinic anhydride to form a polyester reaction product. The described compositions and methods inhibit corrosion by serving as corrosion inhibitor or to passivate a surface or both. The compositions may be used to inhibit or reduce corrosion in various industrial systems.

In some embodiments the reaction is with a hydrocarbon-substituted (e.g., alkyl or alkenyl) carboxylic acid. In some embodiments, the carboxylic acid is a succinic anhydride or succinimide. In some embodiments, the alkyl or alkenyl carboxylic acid is a succinic anhydride or alkyl or alkenyl succinimide. In some embodiments the alkyl or alkenyl is a chain or ring, saturated or unsaturated. In some embodiments, the alkyl or alkenyl is 2-30 carbon atoms, 12-25, 16-30 carbon atoms, or mixtures thereof. In some embodiments, the alkyl or alkenyl are 16-22 carbon atoms.

Any suitable amine may be used to react with the hydrocarbon-substituted (e.g., alkyl or alkenyl) carboxylic acid to result in the described polyester product. The amine may be characterized by the presence of at least one primary, secondary or tertiary amino group.

In some embodiments, the amine is a monoamine, diamine, polyamine or combination thereof. In some embodiments, the amine is a monoamine. In some embodiments the monoamine is ethylamine, dimethylamine, diethylamine, n-butylamine, dibutylamine, allylamine, isobutylamine, cocoamine, stearylamine, laurylamine, methyllaurylamine, oleylamine, N-methyl-octylamine, dodecyl-amine, diethanolamine, morpholine, and octadecyl amine.

In some embodiments, the amine is a diamine, which can include aliphatic diamines, branched aliphatic diamines, cyclic diamines.

In some embodiments, the amine is a polyamine. In some embodiments the polyamine is a hydroxy-containing polyamine. Hydroxy-containing polyamine can be hydroxy monoamines, alkoxylated alkylenepolyamines, e.g., N,N'-(dihydroxyethyl)ethylene diamines. In some embodiments, the polyamine is a condensation reaction between at least one hydroxy compound with at least one polyamine reactant containing at least one primary or secondary amino group. In some embodiments, the hydroxy compounds are polyhydric alcohols and amines. In some embodiments, the hydroxy compounds are polyhydric amines. In some embodiments the polyhydric amine is a monoamine reacted with an alkylene oxide (e.g., ethylene oxide, propylene oxide, butylene oxide) having from two to about 20 carbon atoms. In some embodiments, the hydroxy-containing polyamines are N-(2-hydroxyethyl)ethylenediamine, N,N'-bis(2-hydroxyethyl)ethylenediamine, 1-(2-hydroxyethyl) piperazine, mono(hydroxypropyl)-substituted tetraethylenepentamine, N-(3-hydroxybutyl)tetramethylenediamine, triethanolamine, ethoxylated diethyletriamine (DETA), ethoxylated tetraethylenpentamine(TEPA), ethoxylated pentaethylenehexamine (PEHA).

In some embodiments, the polyhydric amines are diethanolamine, triethanolamine, tri-(hydroxypropyl)amine, tris-(hydroxymethyl)amino methane, 2-amino-2-methyl-1,3-propanediol, N,N,N',N'-tetrakis(2-hydroxypropyl) ethylenediamine, and N,N,N',N'-tetrakis(2-hydroxyethyl) ethylenediamine, ethoxylated triethylenetetramine (TETA).

Any method known to one of skill in the art may be used to prepare the ASA-derived polyesters. In some embodiments, the ratio of the alkyl or alkenyl succinic anhydride to amine alcohol is to open the succinic anhydride ring. In some embodiments, the ratio of the polyhydroxypolyamine to the alkyl or alkenyl succinic anhydride is from 1.1 to about 1:6 or 1:2 to about 1:4. Reactant ratios and temperatures for carrying out such reactions are known to those skilled in the art. In some embodiments the reactions are carried out a temperature from 180° C. to 190° C. for 6-9 hours with a catalyst. In some embodiments, the catalyst used is para-toluene sulfonic acid.

In some embodiments, the composition comprises, consists essentially of or consists of succinic anhydride-derived polyester compounds to inhibit corrosion, the succinic anhydride-derived polyester compounds comprising, consisting essentially of or consisting a polyamine and an alkyl or alkenyl succinic anhydride and having the general formula I:

(Formula I)

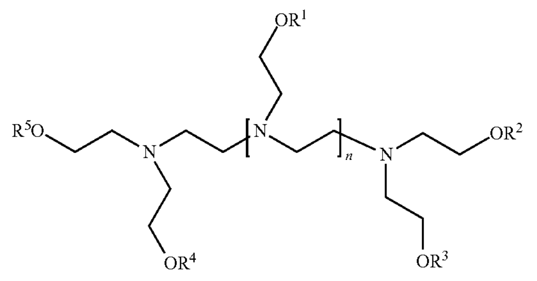

Wherein n is 0-20; and

Wherein $R^1$, $R^2$, $R^3$, $R^4$, and $R^5$ are each individually selected from —H, a ring opened ASA, or cyclic adduct with ASA, wherein at least one of $R^1$, $R^2$, $R^3$, $R^4$, and $R^5$ is an ASA or cyclic adduct with ASA or combination thereof. In some embodiments, the ASA-derived polyesters are formed by the reaction of N,N,N',N'-tetrakis (2-hydroxyethyl)ethylenediamine with ASA. In some embodiments the reaction of N,N,N',N'-tetrakis(2-hydroxyethyl)ethylenediamine with ASA is from 1:1 to 1:4 mole ratio, which produces 1:4 adduct and structures shown below.

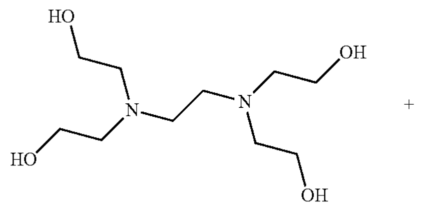

+

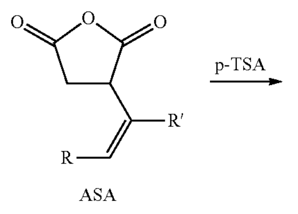

ASA

-continued

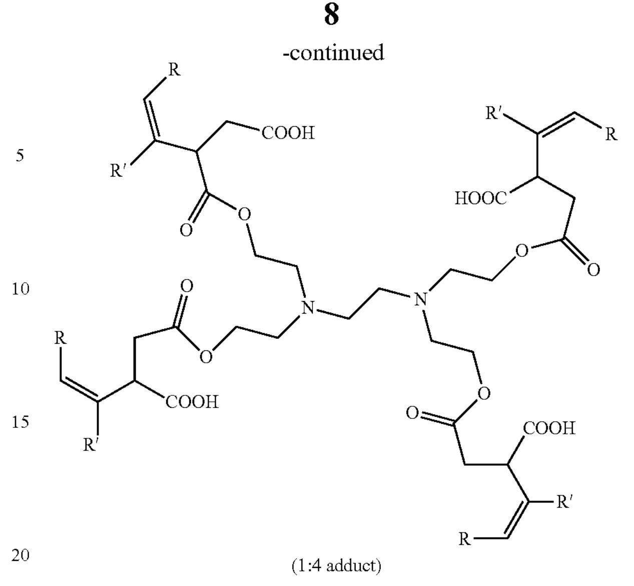

(1:4 adduct)

In some embodiments, the product produced is a mixture of mono-, di-, tri-, tetra-, penta-, and hexa- and higher molecular weight polyesters. In some embodiments, the weight average molecular weight ranges from about 500 gm/mol to about 10,000 gm/mol. In some embodiments, the weight average molecular weight of the polymers may be about 1000 gm/mol, about 1,500 gm/mol, about 2,500 gm/mol, about 5,000 gm/mol, about 10,000 gm/mol, or from about 500-5,000 gm/mol, about 2,000-5,000 gm/mol, about 1,000-5,000 gm/mol or 500-2,000 gm/mol. Molecular weights can be measured or analyzed using conventional methodology familiar to the polymer chemist, including gel permeation chromatography and infrared analysis.

Some of the structures are shown below.

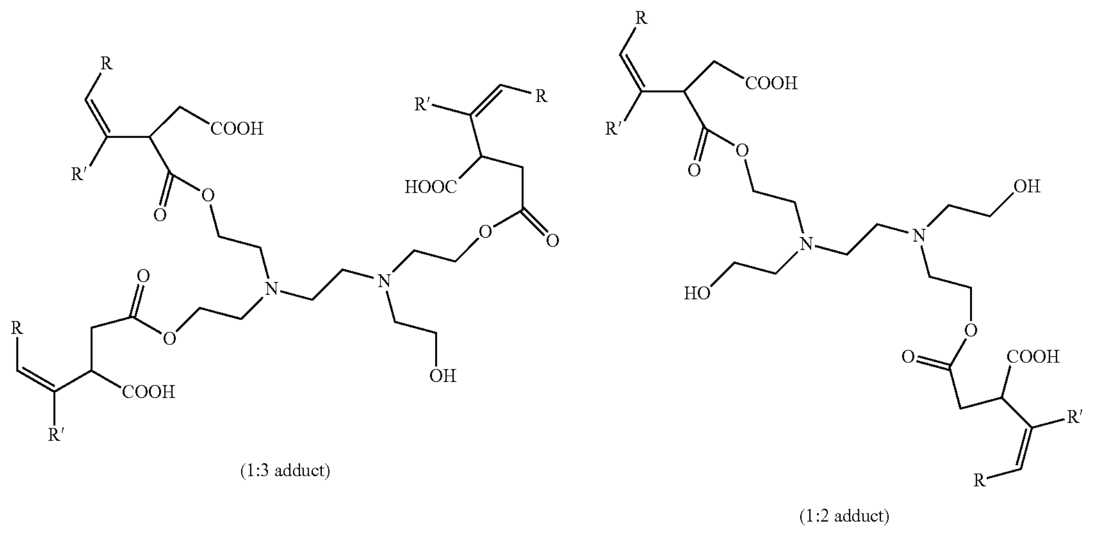

(1:3 adduct)

(1:2 adduct)

-continued
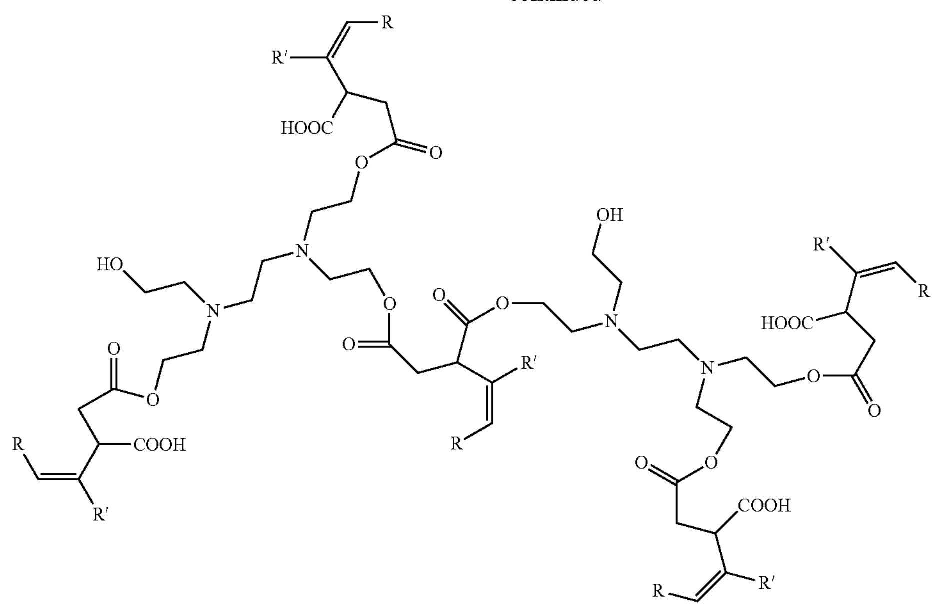
(2:5 adduct)
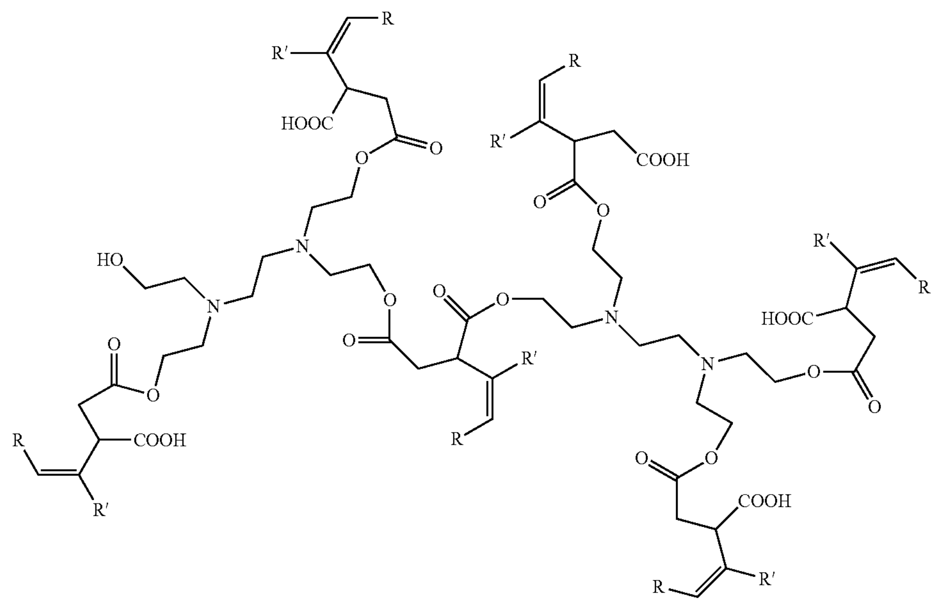
(2:6 adduct)

-continued
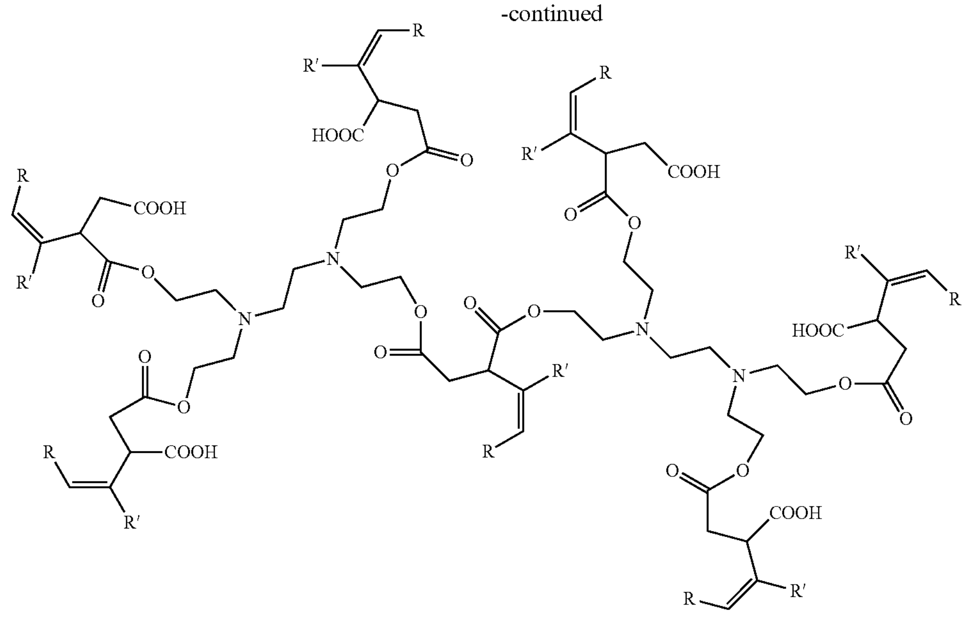
(2:7 adduct)
In some embodiments, cyclic products are also formed as shown below:
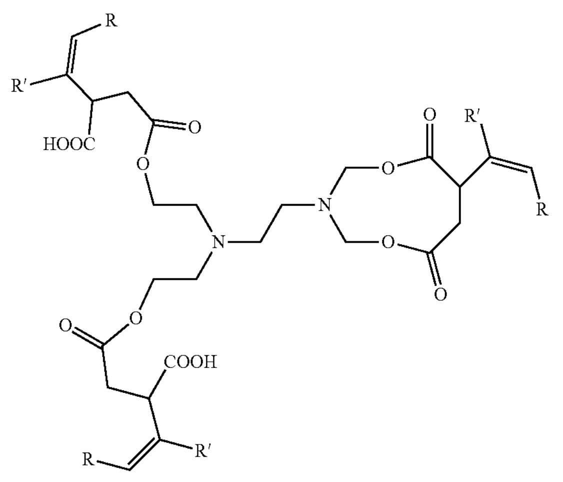
(1:3 cyclic adduct)
-continued
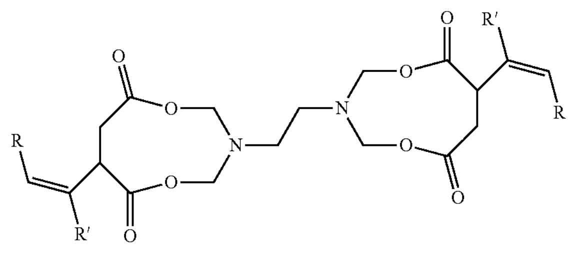
(1:2 dicyclic adduct)
In other embodiments the ASA-derived polyesters are formed by the reaction of ethoxylated triethylenetetramine with ASA in a 1:1 1:6 mole ratio which produces 1:6 adduct and other structures shown below.
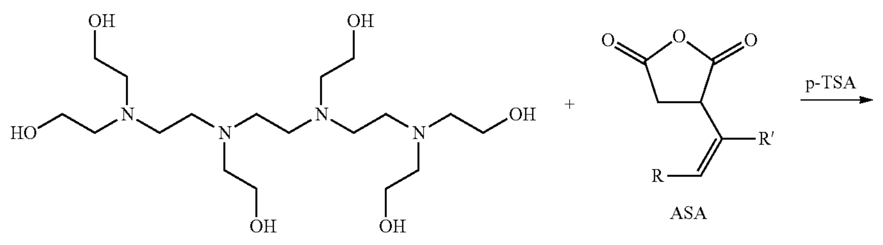

-continued

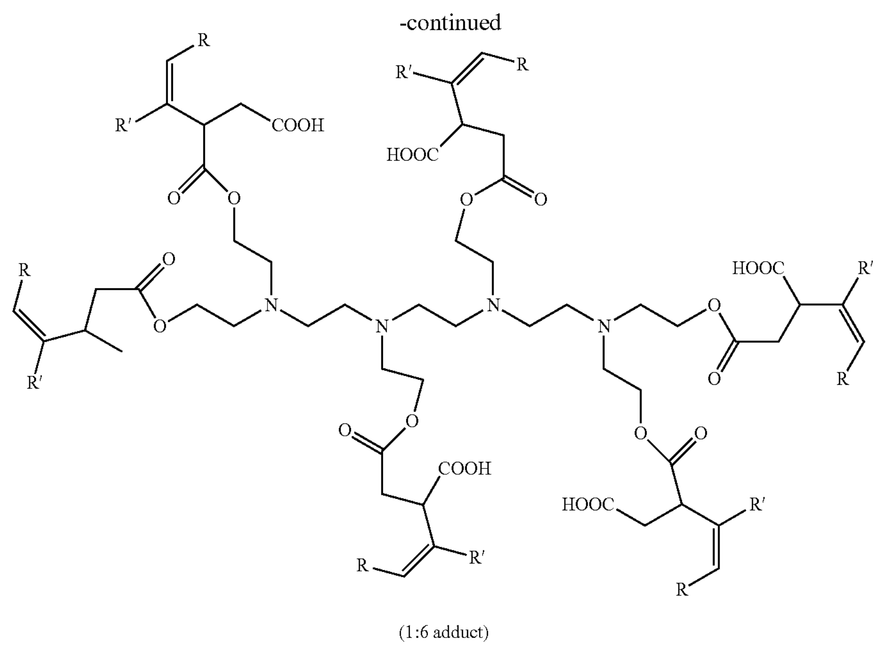

(1:6 adduct)

In some embodiments, the product obtained is a mixture of mono-, di-, tri-, tetra-, penta-, and hexa- and higher molecular weight polyesters. In some embodiments, the weight average molecular weight ranges from about 500 gm/mol to about 10,000 gm/mol. In some embodiments, the weight average molecular weight of the polymers may be about 1000 gm/mol, about 1,500 gm/mol, about 2,500 gm/mol, about 5,000 gm/mol, about 10,000 gm/mol, or from about 500-5,000 gm/mol, about 2,000-5,000 gm/mol, about 1,000-5,000 gm/mol or 500-2,000 gm/mol. Molecular weights can be measured or analyzed using conventional methodology familiar to the polymer chemist, including gel permeation chromatography and infrared analysis.

Additional structures are shown below depending on the ratio of the polyhydroxypolyamine and ASA.

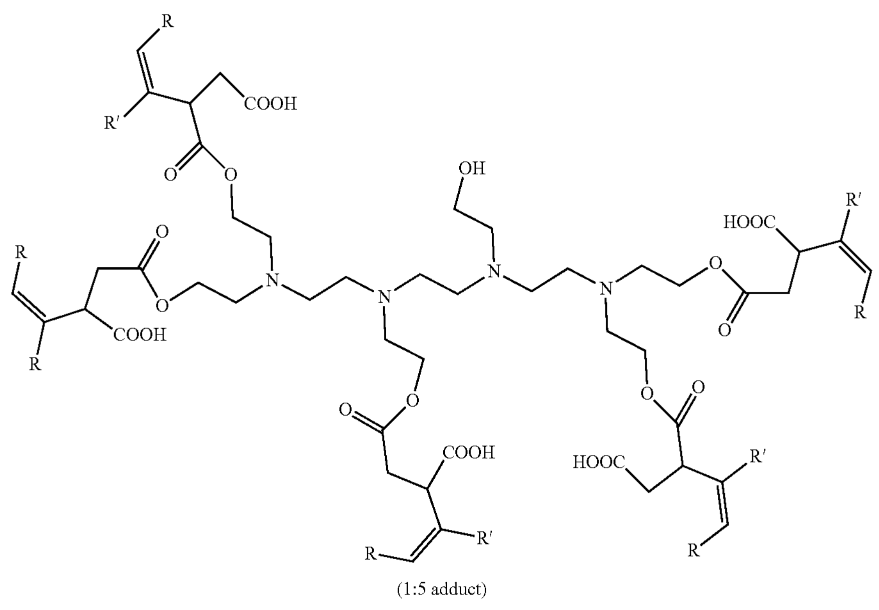

(1:5 adduct)

-continued

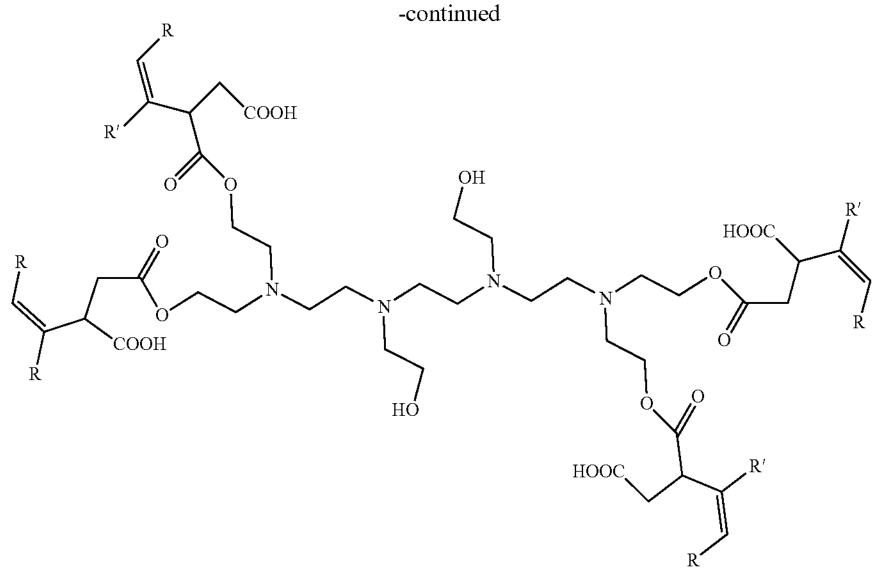

(1:4 adduct)

In any of these structures R and R' are independently selected from hydrocarbon groups, wherein R and R' can be the same or different. In some embodiments, R and R' are independently selected from aliphatic groups. R and R' can have a total number of carbon atoms in the range of 2-30 carbon atoms, 5-25 carbon atoms, 12-25 carbon atoms, or 16-22 carbon atoms. In some embodiments, R has a number of carbon atoms in the range of 1-12, 2-11, 3-10, 4-9, or 5-8. In some embodiments, R' has a number of carbon atoms in the range of 1-14, 2-13, 3-12, 4-11, or 5-10.

In some embodiments the ASA is selected from a succinic acid or succinimide and the alkyl alkenyl portion has C16-C22 and is reacted with a polyamine selected from N,N,N',N'-tetrakis(2-hydroxyethyl)ethylenediamine or an ethoxylated triethylenetetramine (TETA).

The compositions and methods described herein are used to inhibit corrosion. In some embodiments, compositions comprise, consist essentially of, or consist of the described ASA-derived polyesters used for corrosion inhibition. In some embodiments the ASA-derived polyesters are as described in Example 1, wherein R ranges from 16-22 carbons and such compounds are used for corrosion inhibition. In some embodiments, the ASA-derived polyesters are formulated as corrosion inhibitor compositions or as passivation compositions to inhibit corrosion or to passivate a surface or both. Any known method in the art to passivate surfaces can be used, such as for example U.S. Pat. No. 9,845,437, which is incorporated herein by reference in its entirety.

The ASA-derived polyesters are used in methods to passivate the surfaces of process equipment to provide treated process equipment. The treated process equipment mitigates (e.g., inhibits) the corrosion on the metal surfaces. Examples of passivation are also described in U.S. Pat. Nos. 4,024,050, 3,522,093, 6,228,253, ASTM A-967, and ASTM A-380, which references are each incorporated herein in their entirety.

In some embodiments, the ASA-derived polyesters are formulated with a carrier. In some embodiments a carrier in the disclosed ASA-derived polyesters or in a composition can be water, an organic solvent, or a combination of water and an organic solvent. The organic solvent can be an alcohol, a hydrocarbon, a ketone, an ether, an alkylene glycol, a glycol ether, an amide, a nitrile, a sulfoxide, an ester, or a combination thereof. Examples of suitable organic solvents include, but are not limited to, methanol, ethanol, propanol, isopropanol, butanol, 2-ethylhexanol, hexanol, octanol, decanol, 2-butoxyethanol, methylene glycol, ethylene glycol, 1,2-propylene glycol, 1,3-propylene glycol, diethyleneglycol monomethylether, diethylene glycol monoethylether, ethylene glycol monobutyl ether, ethylene glycol dibutyl ether, pentane, hexane, cyclohexane, methylcyclohexane, heptane, decane, dodecane, diesel, toluene, xylene, heavy aromatic naphtha, cyclohexanone, diisobutylketone, diethylether, propylene carbonate, N-methylpyrrolidinone, N,N-dimethylformamide, or a combination thereof.

In some embodiments, the composition can include carriers disclosed U.S. Patent Publication Application Nos. 2019/0062187, which each reference is incorporated herein by reference in its entirety.

In some embodiments, the solvents used to enhance the corrosion performance of the compositions containing the ASA-derived polyesters are sulfur containing compounds. In some embodiments the other sulfur-containing compounds are, thioglycolic acid, 3,3'-dithiodipropionic acid, thiosulfate, thiourea, 2-mercaptoethanol, L-cysteine, and tert-butyl mercaptan.

The compositions can comprise from about 1 wt-% to about 80 wt-%, from about 1 wt-% to about 70 wt-%, from about 1 wt-% to about 60 wt-%, from about 1 wt-% to about 50 wt-%, from about 1 wt-% to about 40 wt-%, from about 1 wt-% to about 30 wt-%, from about 1 wt-% to about 20 wt-%, from about 1 wt-% to about 10 wt-%, from about 5 wt-% to about 10 wt-%, from about 5 wt-% to about 20 wt-%, from about 5 wt-% to about 30 wt-%, from about 5 wt-% to about 40 wt-%, from about 5 wt-% to about 50 wt-%, from about 10 wt-% to about 20 wt-%, from about 10 wt-% to about 30 wt-%, from about 10 to about 40 wt-%, from about 10 wt-% to about 50 wt-%, about 10 wt-%, about 20 wt-%, about 30 wt-%, about 40-%, about 50 wt-%, about 60 wt-%, about 70 wt-%, about 80 wt-%, about 90 wt-%, or any value there between of the one or more carrier, based on total weight of the composition.

In some embodiments, the ASA-derived polyesters or compositions containing them include other additives such as one or more asphaltene inhibitors, paraffin inhibitors, scale inhibitors, demulsifiers, water clarifiers, dispersants, emulsion breakers, antifoams, carriers, acid, biocide, other corrosion inhibitors, fouling control agent, antioxidant, polymer degradation prevention agent, permeability modifier, foaming agent, antifoaming agent, fracturing proppant, scavenger for $H_2S$, $CO_2$, and/or $O_2$, gelling agent, lubricant, and friction reducing agent, salt, organic sulfur compound, water clarifier, emulsion breaker, reverse emulsion breaker, gas hydrate inhibitor, a pH modifier, a surfactant, sequestrant, solubilizer, lubricant, buffer, cleaning agent, rinse aid, preservative, binder, thickener or other viscosity modifier, processing aid, carrier, water-conditioning agent, or foam generator, threshold agent or system, aesthetic enhancing agent (e.g., dye, odorant, perfume), or other additive suitable for formulation with a reverse emulsion breaker, or any combinations thereof.

One of skill in the art will appreciate that the composition disclosed herein will vary according to the specific corrosion composition being manufactured and its intended use. Examples of the other additives an also be found in US Patent Publication Application No. 2019/0062187, which reference is incorporated herein by reference in its entirety.

Biocides suitable for use may be oxidizing or non-oxidizing biocides. Oxidizing biocides include, but are not limited to, bleach, chlorine, bromine, chlorine dioxide, and materials capable of releasing chlorine and bromine. Non-oxidizing biocides include, but are not limited to, glutaraldehyde, isothiazolin, 2,2-dibromo-3-nitrilopropionamide, 2-bromo-2-nitropropane-1,3 diol, 1-bromo-1-(bromomethyl)-1,3-propanedicarbonitrile, tetrachloroisophthalonitrile, alkyldimethylbenzylammonium chloride, dimethyl dialkyl ammonium chloride, didecyl dimethyl ammonium chloride, poly(oxyethylene(dimethyliminio)ethylene(dimethyliminio)ethylene dichloride, methylene bisthiocyanate, 2-decylthioethanamine, tetrakishydroxymethyl phosphonium sulfate, dithiocarbamate, cyanodithioimidocarbonate, 2-methyl-5-nitroimidazole-1-ethanol, 2-(2-bromo-2-nitroethenyl)furan, beta-bromo-beta-nitrostyrene, beta-nitrostyrene, beta-nitrovinyl furan, 2-bromo-2-bromomethyl glutaronitrile, bis(trichloromethyl) sulfone, S-(2-hydroxypropyl)thiomethanesulfonate, tetrahydro-3,5-dimethyl-2H-1,3,5-hydrazine-2-thione, 2-(thiocyanomethylthio)benzothiazole, 2-bromo-4'-hydroxyacetophenone, 1,4-bis(bromoacetoxy)-2-butene, bis(tributyltin)oxide, 2-(tert-butylamino)-4-chloro-6-(ethylamino)-s-triazine, dodecylguanidine acetate, dodecylguanidine hydrochloride, coco alkyldimethylamine oxide, n-coco alkyltrimethylenediamine, tetra-alkyl phosphonium chloride, 7-oxabicyclo[2.2.1]heptane-2,3-dicarboxylic acid, 4,5-dichloro-2-n-octyl-4-isothiazoline-3-one, 5-chloro-2-methyl isothiazolin-3-one and 2-methyl-4-isothiazolin-3-one.

Suitable non-oxidizing biocides also include, for example, aldehydes (e.g., formaldehyde, glutaraldehyde, and acrolein), amine-type compounds (e.g., quaternary amine compounds and cocodiamine), halogenated compounds (e.g., 2-bromo-2-nitropropane-3-diol (Bronopol) and 2 dibromo-3-nitrilopropionamide (DBNPA)), sulfur compounds (e.g., isothiazolone, carbamates, and metronidazole), and quaternary phosphonium salts (e.g., tetrakis(hydroxymethyl)-phosphonium sulfate (THPS)).

Suitable oxidizing biocides include, for example, sodium hypochlorite, trichloroisocyanuric acids, dichloroisocyanuric acid, calcium hypochlorite, lithium hypochlorite, chlorinated hydantoins, stabilized sodium hypobromite, activated sodium bromide, brominated hydantoins, chlorine dioxide, ozone, peroxycarboxylic acid, peroxycarboxylic acid composition, and peroxides.

The ASA-derived polyesters or in a composition can comprise from about 0.1 wt-% to about 10 wt-%, from about 0.5 wt-% to about 5 wt-%, or from about 0.5 wt-% to about 4 wt-% of a biocide, based on total weight of the composition. In some embodiments, the ASA-derived polyesters or in a composition is free of a biocide. In some embodiments, the ASA-derived polyesters or in a composition is free of an oxidizing biocide. In some other embodiments, the ASA-derived polyesters or in a composition is free of a non-oxidizing biocide.

In some embodiments, the ASA-derived polyesters or in a composition can further comprise a dispersant. A dispersant keeps particulate matter present in the water of a water system dispersed, so that it does not agglomerate. The composition can comprise from about 0.1 to 10 wt-%, from about 0.5 to 5 wt-%, or from about 0.5 to 4 wt-% of a dispersant, based on total weight of the composition.

A dispersant may be an acrylic acid polymer, maleic acid polymer, copolymer of acrylic acid with sulfonated monomers, alkyl esters thereof, or combination thereof. These polymers may include terpolymers of acrylic acid, acrylamide and sulfonated monomers. These polymers may also include quad-polymers consisting of acrylic acid and three other monomers.

In some embodiments, the dispersants include, but are not limited to, aliphatic phosphonic acids with 2-50 carbons, such as hydroxyethyl diphosphonic acid, and aminoalkyl phosphonic acids, e.g., polyaminomethylene phosphonates with 2-10 N atoms e.g., each bearing at least one methylene phosphonic acid group; examples of the latter are ethylenediamine tetra(methylene phosphonate), diethylenetriamine penta(methylene phosphonate), and the triamine- and tetramine-polymethylene phosphonates with 2-4 methylene groups between each N atom, at least 2 of the numbers of methylene groups in each phosphonate being different. Other suitable dispersion agents include lignin, or derivatives of lignin such as lignosulfonate and naphthalene sulfonic acid and derivatives.

In some embodiments, the dispersant in the ASA-derived polyesters or in a composition s disclosed herein is a reaction product of tall oil fatty acids with diethylenetriamine and acrylic acid (1:1:1), reaction product of fatty acids or tall-oil with triethylenetetramine or tetraethylenepentamine, reaction product of diethylenetriamine and napthenic acid.

The ASA-derived polyesters or in a composition can further comprise an organic sulfur compound, such as a mercaptoalkyl alcohol, mercaptoacetic acid, thioglycolic acid, 3,3'-dithiodipropionic acid, sodium thiosulfate, thiourea, L-cysteine, tert-butyl mercaptan, sodium thiosulfate, ammonium thiosulfate, sodium thiocyanate, ammonium thiocyanate, sodium metabisulfite, or a combination thereof. In some embodiments, the mercaptoalkyl alcohol comprises 2-mercaptoethanol. Such compounds are used as synergists in the composition.

In some embodiments, the organic sulfur compound in the ASA-derived polyesters or in a composition is 2 Mercaptoethanol, sodium thiosulfate, thioglycolic acid, or a mixture thereof.

The organic sulfur compound can constitute from about 0.5 wt-% to about 15 wt-% of the composition, based on total weight of the composition. In some embodiments, organic sulfur compound can constitute from about 1 wt-% to about 10 wt-% and more. In other embodiments, the organic sulfur compound can constitute from about 1 wt-% to about 5 wt-%. The organic sulfur compound can constitute about 1 wt-%, about 2 wt-%, about 3 wt-%, about 4 wt-%, about 5 wt-%, about 6 wt-%, about 7 wt-%, about 8 wt-%, about 9 wt-%, about 10 wt-%, about 11 wt-%, about 12 wt-%, about 13 wt-%, about 14 wt-%, or about 15 wt-% of the composition.

The ASA-derived polyesters or in a composition can further comprise a de-emulsifier. In some embodiments, the demulsifier comprises an oxyalkylate polymer, such as a polyalkylene glycol. The de-emulsifier can constitute from about 0.1 wt-% to about 10 wt-%, from about 0.5 wt-% to about 5 wt. %, or from about 0.5 wt-% to about 4 wt-% of the composition, based on total weight of the composition. The de-emulsifier can constitute about 0.5 wt-%, about 1 wt-%, about 1.5 wt-%, about 2 wt-%, about 2.5 wt-%, about 3 wt-%, about 3.5 wt-%, about 4 wt-%, about 4.5 wt-%, or about 5 wt-% of the composition.

The ASA-derived polyesters or in a composition can further comprise an asphaltene inhibitor. The composition can comprise from about 0.1 wt-% to about 10 wt-%, from about 0.1 wt-% to about 5 wt-%, or from about 0.5 wt-% to about 4 wt-% of an asphaltene inhibitor, based on total weight of the composition. Suitable asphaltene inhibitors include, but are not limited to, aliphatic sulfonic acids; alkyl aryl sulfonic acids; aryl sulfonates; lignosulfonates; alkylphenol/aldehyde resins and similar sulfonated resins; polyolefin esters; polyolefin imides; polyolefin esters with alkyl, alkylenephenyl or alkylenepyridyl functional groups; polyolefin amides; polyolefin amides with alkyl, alkylenephenyl or alkylenepyridyl functional groups; polyolefin imides with alkyl, alkylenephenyl or alkylenepyridyl functional groups; alkenyl/vinyl pyrrolidone copolymers; graft polymers of polyolefins with maleic anhydride or vinyl imidazole; hyperbranched polyester amides; polyalkoxylated asphaltenes, amphoteric fatty acids, salts of alkyl succinates, sorbitan monooleate, and polyisobutylene succinic anhydride.

The ASA-derived polyesters or in a composition can further comprise a paraffin inhibitor. The composition can comprise from about 0.1 wt-% to about 10 wt-%, from about 0.1 wt-% to about 5 wt-%, or from about 0.5 wt-% to about 4 wt-% of a paraffin inhibitor, based on total weight of the composition. Suitable paraffin inhibitors include, but are not limited to, paraffin crystal modifiers, and dispersant/crystal modifier combinations. Suitable paraffin crystal modifiers include, but are not limited to, alkyl acrylate copolymers, alkyl acrylate vinylpyridine copolymers, ethylene vinyl acetate copolymers, maleic anhydride ester copolymers, branched polyethylenes, naphthalene, anthracene, microcrystalline wax and/or asphaltenes. Suitable paraffin dispersants include, but are not limited to, dodecyl benzene sulfonate, oxyalkylated alkylphenol s, and oxyalkylated alkylphenolic resins.

The ASA-derived polyesters or in a composition can further comprise a scale inhibitor. The composition can comprise from about 0.1 wt-% to about 20 wt-%, from about 0.5 wt-% to about 10 wt-%, or from about 1 wt-% to about 10 wt-% of a scale inhibitor, based on total weight of the composition. Suitable scale inhibitors include, but are not limited to, phosphates, phosphate esters, phosphoric acids, phosphonates, phosphonic acids, polyacrylamides, salts of acrylamidomethyl propane sulfonate/acrylic acid copolymer (AMPS/AA), phosphinated maleic copolymer (PHOS/MA), mono-, bis- and oligomeric phosphinosuccinic acid (PSO) derivatives, polycarboxylic acid, hydrophobically modified polycarboxylic acid, and salts of a polymaleic acid/acrylic acid/acrylamidomethyl propane sulfonate terpolymer (PMA/AA/AMPS).

The ASA-derived polyesters or in a composition can further comprise an emulsifier. The composition can comprise from about 0.1 wt-% to about 10 wt-%, from about 0.5 wt-% to about 5 wt-%, or from about 0.5 wt-% to about 4 wt-% of an emulsifier, based on total weight of the composition. Suitable emulsifiers include, but are not limited to, salts of carboxylic acids, products of acylation reactions between carboxylic acids or carboxylic anhydrides and amines, and alkyl, acyl and amide derivatives of saccharides (alkyl-saccharide emulsifiers).

The ASA-derived polyesters or in a composition can further comprise a water clarifier. The composition can comprise from about 0.1 wt-% to about 10 wt-%, from about 0.5 wt-% to about 5 wt-%, or from about 0.5 wt-% to about 4 wt-% of a water clarifier, based on total weight of the composition. Suitable water clarifiers include, but are not limited to, inorganic metal salts such as alum, aluminum chloride, and aluminum chlorohydrate, or organic polymers such as acrylic acid-based polymers, acrylamide-based polymers, polymerized amines, alkanolamines, thiocarbamates, and cationic polymers such as diallyldimethylammonium chloride (DADMAC).

The ASA-derived polyesters or in a composition can further comprise an emulsion breaker. The composition can comprise from about 0.1 wt-% to about 10 wt-%, from about 0.5 wt-% to about 5 wt-%, or from about 0.5 wt-% to about 4 wt-% of an emulsion breaker, based on total weight of the composition. Suitable emulsion breakers include, but are not limited to, dodecylbenzylsulfonic acid (DDBSA), the sodium salt of xylenesulfonic acid (NAXSA), epoxylated and propoxylated compounds, and resins, such as phenolic and epoxide resins.

The ASA-derived polyesters or in a composition can further comprise a hydrogen sulfide scavenger. The composition can comprise from about 1 wt-% to about 50 wt-%, from about 1 wt-% to about 40 wt-%, from about 1 wt-% to about 30 wt-%, from about 0.1 wt-% to about 10 wt-%, from about 0.5 wt-% to about 5 wt-%, or from about 0.5 wt-% to about 4 wt-% of a hydrogen sulfide scavenger, based on total weight of the composition. Suitable additional hydrogen sulfide scavengers include, but are not limited to, oxidants (e.g., inorganic peroxides such as sodium peroxide or chlorine dioxide); aldehydes (e.g., of 1-10 carbons such as formaldehyde, glyoxal, glutaraldehyde, acrolein, or methacrolein; triazines (e.g., monoethanolamine triazine, monomethylamine triazine, and triazines from multiple amines or mixtures thereof); condensation products of secondary or tertiary amines and aldehydes, and condensation products of alkyl alcohols and aldehydes.

The ASA-derived polyesters or in a composition can further comprise a gas hydrate inhibitor. The composition can comprise from about 0.1 wt-% to about 25 wt-%, from about 0.5 wt-% to about 20 wt-%, from about 1 wt-% to about 10 wt-%, from about 0.1 wt-% to about 10 wt-%, from about 0.5 wt-% to about 5 wt-%, or from about 0.5 wt-% to about 4 wt-% of a gas hydrate inhibitor, based on total weight of the composition. Suitable gas hydrate inhibitors include, but are not limited to, thermodynamic hydrate inhibitors (THI), kinetic hydrate inhibitors (KHI), and anti-agglomerates (AA). Suitable thermodynamic hydrate inhibitors include, but are not limited to, sodium chloride, potassium chloride, calcium chloride, magnesium chloride, sodium bromide, formate brines (e.g., potassium formate), polyols (such as glucose, sucrose, fructose, maltose, lactose, gluconate, monoethylene glycol, diethylene glycol, triethylene glycol, mono-propylene glycol, dipropylene glycol, tripropylene glycols, tetrapropylene glycol, monobutylene glycol, dibutylene glycol, tributylene glycol, glycerol, diglycerol, triglycerol, and sugar alcohols (e.g., sorbitol, mannitol)), methanol, propanol, ethanol, glycol ethers (such as diethyleneglycol monomethylether, ethyleneglycol monobutylether), and alkyl or cyclic esters of alcohols (such as ethyl lactate, butyl lactate, methylethyl benzoate).

The ASA-derived polyesters or in a composition can further comprise a kinetic hydrate inhibitor. The composition can comprise from about 0.1 wt-% to about 25 wt-%, from about 0.5 wt-% to about 20 wt-%, from about 1 wt-% to about 10 wt-%, from about 0.1 wt-% to about 10 wt-%, from about 0.5 wt-% to about 5 wt-%, or from about 0.5 wt-% to about 4 wt-% of a kinetic hydrate inhibitor, based on total weight of the composition. Suitable kinetic hydrate inhibitors and anti-agglomerates include, but are not limited to, polymers and copolymers, polysaccharides (such as hydroxyethylcellulose (HEC), carboxymethylcellulose (CMC), starch, starch derivatives, and xanthan), lactams (such as polyvinylcaprolactam, polyvinyl lactam), pyrrolidones (such as polyvinyl pyrrolidone of various molecular weights), fatty acid salts, ethoxylated alcohols, propoxylated alcohols, sorbitan esters, ethoxylated sorbitan esters, polyglycerol esters of fatty acids, alkyl glucosides, alkyl polyglucosides, alkyl sulfates, alkyl sulfonates, alkyl ester sulfonates, alkyl aromatic sulfonates, alkyl betaine, alkyl amido betaines, hydrocarbon based dispersants (such as lignosulfonates, iminodisuccinates, polyaspartates), amino acids, and proteins.

The ASA-derived polyesters or in a composition can further comprise a pH modifier. The composition can comprise from about 0.1 wt-% to about 20 wt-%, from about 0.5 wt-% to about 10 wt-%, or from about 0.5 wt-% to about 5 wt-% of a pH modifier, based on total weight of the composition. Suitable pH modifiers include, but are not limited to, alkali hydroxides, alkali carbonates, alkali bicarbonates, alkaline earth metal hydroxides, alkaline earth metal carbonates, alkaline earth metal bicarbonates and mixtures or combinations thereof. Exemplary pH modifiers include sodium hydroxide, potassium hydroxide, calcium hydroxide, calcium oxide, sodium carbonate, potassium carbonate, sodium bicarbonate, potassium bicarbonate, magnesium oxide, and magnesium hydroxide.

The ASA-derived polyesters or in a composition can further comprise a surfactant. The composition can comprise from about 0.1 wt-% to about 10 wt-%, from about 0.5 wt-% to about 5 wt-%, or from about 0.5 wt-% to about 4 wt-% of a surfactant, based on total weight of the composition. A suitable surfactant can be a nonionic, semi-nonionic, cationic, anionic, amphoteric, zwitterionic, Gemini, di-cationic, di-anionic surfactant, or mixtures thereof. Anionic surfactants include alkyl aryl sulfonates, olefin sulfonates, paraffin sulfonates, alcohol sulfates, alcohol ether sulfates, alkyl carboxylates and alkyl ether carboxylates, and alkyl and ethoxylated alkyl phosphate esters, and mono and dialkyl sulfosuccinates and sulfosuccinamates. Nonionic surfactants include alcohol alkoxylates, alkylphenol alkoxylates, block copolymers of ethylene, block copolymers of ethylene and propylene, propylene and butylene oxides, alkyl dimethyl amine oxides, alkyl-bis(2-hydroxyethyl) amine oxides, alkyl amidopropyl dimethyl amine oxides, alkylamidopropyl-bis (2-hydroxyethyl) amine oxides, alkyl polyglucosides, polyalkoxylated glycerides, sorbitan esters and polyalkoxylated sorbitan esters, and alkoyl polyethylene glycol esters and diesters. Also included are betaines and sultanes, amphoteric surfactants such as alkyl amphoacetates and amphodiacetates, alkyl amphopropionates and amphodipropionates, and alkyliminodipropionate.

In some embodiments, the surfactant is phosphate esters of ethoxylated C10-C16 alcohols, ethoxylated C11-C14 iso or C13 rich phosphates, ethoxylated nonylphenol, ethoxylated branched nonylphenol, or mixture thereof. In some embodiments, the ASA-derived polyesters further comprise one or more solvents or a mixture thereof. In some embodiments, a composition which includes solvents suitable for formulation of the ASA-derived polyesters are water, brine, seawater, alcohols such as methanol, ethanol, isopropanol, n-propanol, n-butanol, isobutanol, sec-butanol, t-butanol or higher alcohols such as benzyl alcohol); ketones such as acetone, or methylethyl ketone (2-butanone); acetonitrile; esters such as ethyl acetate, propyl acetate and butyl acetate; ethers such as diethylether or higher, e.g., methyl t-butyl ether, glyme, diglyme, ethylene glycol monobutyl ether, ethylene diglycol ethylether, 1,4 dioxane and related; aromatics such as toluene, xylene(s), diethylbenzene, naphthalene and related aromatics or refinery cuts (heavy aromatic naptha, heavy aromatic distillates, and related); aliphatics such as pentane, hexane, heptane, octane, or refined gasoline; or several "green" solvents such as 2-methyltetrahydrofuran, furfural alcohol, and cyclopentylmethylether.

In some embodiments, the ASA-derived polyesters are provided neat (viz., without a solvent). In some embodiments, the ASA-derived polyesters include dissolving or dispersing the ASA-derived polyesters in water or water mixed with a water-soluble solvent before applying the ASA-derived polyesters. In some embodiments, the ASA-derived polyesters are provided as a concentrate. In some embodiments, the method includes applying an ASA-derived polyester concentrate directly to a metal containment in an amount that results in 0.1 ppm to 10,000 ppm; 0.1 ppm to 5000 ppm; or 0.1 ppm to 1000 ppm (by weight or by volume) of the ASA-derived polyesters in the fluid source. In other embodiments the method further includes diluting ASA-derived polyesters concentrate prior to introducing the ASA-derived polyesters. Diluting comprises, consists essentially of, or consists of combining ASA-derived polyesters concentrate with a diluent, wherein the diluent comprises, consists essentially of, or consists of water, a water source, a water-soluble solvent, or a mixture of two or more thereof; and optionally includes mixing the ASA-derived polyesters concentrate with the diluent prior to the introducing of the ASA-derived polyesters to the fluid source. In some embodiments, the ASA-derived polyesters or in a composition is used in a method of inhibiting corrosion in a fluid source. The fluid source can be contained in a metal container or in contact with pipelines used to transport fluid sources toward, into, out of a subterranean formation. In some embodiments, the fluid source contains corrodents. In some embodiments, the corrodents include hydrogen sulfide, carbon dioxide, oxygen, sodium chloride, calcium chloride, sulfur dioxide, or combination thereof. In some embodiments, the fluid source comprises water, gas, and liquid hydrocarbon or combinations thereof. In some embodiments, the fluid source is produced water or an injectate. In some embodiments, the metal containment is a tank, pipe, or other apparatus having a metal surface in contact with a fluid source, or potentially in contact with a fluid source, wherein the fluid source includes one or more corrodents.

In some embodiments, the pH of the fluid source is less than 7. In some embodiments, the pH of the fluid source is between about 1 and about 6, between 5 and 6, between 4 and 5, between 3 and 4, between 2 and 3, between 1 and 2, or between 0 and 1.

In some embodiments, the composition comprising the ASA-derived polyesters is applied to a fluid source that contains various levels of water cut. One of ordinary skill in the art understands that "water cut" refers to the water percentage in a hydrocarbon phase (e.g., oil) and water mixture. In some embodiments, the water cut is from about 1% to about 80% w/w with respect to the hydrocarbon phase. In other embodiments, the water cut is from about 1% to about 30% w/w, from about 5% to about 40% w/w, from about 10% to about 60% w/w, from about 15% to about 80% w/w with respect to the hydrocarbon phase.

In some embodiments, the ASA-derived polyesters or in a composition is applied to a fluid source that contains various levels of salinity. In some embodiments, the fluid source has a salinity of about 0.1% to about 25% or about 10% to about 25% weight/weight (w/w) total dissolved solids.

In other embodiments the ASA-derived polyesters or in a composition is applied to a fluid source that contains fresh water, recycled water, salt water, surface water, produced water, an injectate, a liquid hydrocarbon or a mixture thereof.

In some embodiments, the methods of inhibiting corrosion are in a water system. In some embodiments the water system is a cooling water system, a boiler water system, a petroleum well, a downhole formation, a geothermal well, a mineral washing system, a flotation and benefaction system, a papermaking system, a gas scrubber, an air washer, a continuous casting process in the metallurgical industry, an air conditioning and refrigeration system, a water reclamation system, a water purification system, a membrane filtration system, a food processing system, a clarifier system, a municipal sewage treatment system, a municipal water treatment system, or a potable water system or any storage, and refining equipment such as pipes, transfer lines, valves, and the like. Additional systems that the ASA-derived polyesters or in a composition can be applied to are as described in US Patent Publication Application No. 2019/0062187, which reference is incorporated herein by reference in its entirety. The ASA-derived polyesters or in a composition can be introduced can be an aqueous medium. The aqueous medium can comprise water, gas, and optionally liquid hydrocarbon.

A fluid to which the ASA-derived polyesters or in a composition can be introduced can be a liquid hydrocarbon. The liquid hydrocarbon can be any type of liquid hydrocarbon including, but not limited to, crude oil, heavy oil, processed residual oil, bituminous oil, coker oils, coker gas oils, fluid catalytic cracker feeds, gas oil, naphtha, fluid catalytic cracking slurry, diesel fuel, fuel oil, jet fuel, gasoline, and kerosene. The fluid or gas can be a refined hydrocarbon product.

A fluid or gas treated with the ASA-derived polyesters or in a composition can be at any selected temperature, such as ambient temperature or an elevated temperature. The fluid (e.g., liquid hydrocarbon) or gas can be at a temperature of from about 40° C. to about 250° C. The fluid or gas can be at a temperature of from about −50° C. to about 300° C., from about 0° C. to about 200° C., from about 10° C. to about 100° C., or from about 20° C. to about 90° C. The fluid or gas can be at a temperature of about 22° C., about 23° C., about 24° C., about 25° C., about 26° C., about 27° C., about 28° C., about 29° C., about 30° C., about 31° C., about 32° C., about 33° C., about 34° C., about 35° C., about 36° C., about 37° C., about 38° C., about 39° C., or about 40° C. The fluid or gas can be at a temperature of about 85° C., about 86° C., about 87° C., about 88° C., about 89° C., about 90° C., about 91° C., about 92° C., about 93° C., about 94° C., about 95° C., about 96° C., about 97° C., about 98° C., about 99° C., or about 100° C.

The fluid or gas of a water system or the water of a water system, in which the ASA-derived polyesters or in a composition are introduced, can be contained in and/or exposed to many types of apparatuses. For example, the fluid or gas can be contained in an apparatus that transports fluid or gas from one point to another, such as an oil and/or gas pipeline. The apparatus can be part of an oil and/or gas refinery, such as a pipeline, a separation vessel, a dehydration unit, or a gas line. The fluid can be contained in and/or exposed to an apparatus used in oil extraction and/or production, such as a wellhead. The apparatus can be part of a coal-fired power plant. The apparatus can be a scrubber (e.g., a wet flue gas desulfurizer, a spray dry absorber, a dry sorbent injector, a spray tower, a contact or bubble tower, or the like). The apparatus can be a cargo vessel, a storage vessel, a holding tank, or a pipeline connecting the tanks, vessels, or processing units.

The ASA-derived polyesters or in a composition can be introduced into a fluid or gas of the water system by any appropriate method for ensuring dispersal through the fluid or gas. For examples, the ASA-derived polyesters or in a composition can be added to the hydrocarbon fluid before the hydrocarbon fluid contacts the surface.

The ASA-derived polyesters or in a composition can be added at a point in a flow line upstream from the point at which corrosion control is desired. The ASA-derived polyesters or in a composition can be injected using mechanical equipment such as chemical injection pumps, piping tees, injection fittings, atomizers, quills, and the like.

The ASA-derived polyesters or in a composition can be pumped into an oil and/or gas pipeline using an umbilical line. A capillary injection system can be used to deliver the ASA-derived polyesters or in a composition to a selected fluid.

A fluid to which the ASA-derived polyesters or in a composition can be introduced can be an aqueous medium. The aqueous medium can comprise water, gas, and optionally liquid hydrocarbon. A fluid to which the ASA-derived polyesters or in a composition can be introduced can be a liquid hydrocarbon.

The ASA-derived polyesters or in a composition can be introduced into a liquid and a mixture of several liquids, a liquid and gas, liquid, solid, and gas. The ASA-derived polyesters or in a composition can be injected into a gas stream as an aqueous or non-aqueous solution, mixture, or slurry.

The fluid or gas can be passed through an absorption tower comprising the ASA-derived polyesters or in a composition or the di-cationic or di-anionic compounds.

The ASA-derived polyesters or in a composition can be applied to a fluid or gas to provide any selected concentration. The ASA-derived polyesters or in a composition are typically added to a flow line to provide an effective treating dose of the ASA-derived polyesters or in a composition from about 0.1 ppm to 10,000 ppm; from 0.1 ppm to 5,000 ppm; from 0.1 ppm to 100; from about 100 ppm to 1000 ppm; from about 500 ppm to 3000 ppm; from about 750 ppm to 3,000 ppm; from about 5000 ppm to 2,000 ppm; from about 5000 ppm to 3,000 ppm; from about 100 ppm to 3,000 ppm; from about 1 ppm to 100 ppm, from about 10 ppm to 50 ppm; from about 50 ppm to 100 ppm, from about 1 ppm to 50 ppm; from about 1 ppm to 20 ppm; from about 1 ppm to 5 ppm; from about 3 ppm to 20 ppm; from 0.1 ppm to 5 ppm; or from about 0.1 ppm to 1 ppm by weight or volume of the ASA-derived polyesters in the fluid source.

The ASA-derived polyesters or in a composition can be applied continuously, in batch, or a combination thereof. The ASA-derived polyesters or in a composition dosing can be continuous. The ASA-derived polyesters or in a composition dosing can be intermittent (e.g., batch treatment) or can be continuous/maintained and/or intermittent.

Dosage rates for continuous treatments typically range from about 1-10 ppm to about 500 ppm, or about 10 ppm to about 200 ppm. Dosage rates for batch treatments typically range from about 10 ppm to about 400,000 ppm, or about 10 ppm to about 20,000 ppm. The ASA-derived polyesters or in a composition can be applied as a pill to a pipeline, providing a high dose (e.g., 20,000 ppm) of the composition.

The flow rate of a flow line in which the ASA-derived polyesters or in a composition is used can be between about 0.1 feet per second and about 1,000 feet per second, or between about 0.1 feet per second and about 50 feet per second. The ASA-derived polyesters or in a composition can also be formulated with water to facilitate addition to the flow line.

In some embodiments, the ASA-derived polyesters or in a composition are used in an amount from about 0.1 ppm to 10,000 ppm; from about 0.1 ppm to 5,000 ppm; from about 0.1 ppm to 1,000 ppm; from about 100 ppm to 1000 ppm; from about 500 ppm to 3000 ppm; from about 750 ppm to 3,000 ppm; from about 5000 ppm to 2,000 ppm; from about 5000 ppm to 3,000 ppm; from about 100 ppm to 3,000 ppm; from about 1 ppm to 100 ppm, from about 10 ppm to 50 ppm; from about 50 ppm to 100 ppm, from about 1 ppm to 50 ppm; from about 1 ppm to 20 ppm; from about 1 ppm to 5 ppm; from about 3 ppm to 20 ppm; from 0.1 ppm to 5 ppm; or from about 0.1 ppm to 1 ppm by weight or volume of the ASA-derived polyesters in the fluid source.

In some embodiments, various dosage amounts of the composition and/or the ASA-derived polyesters are introduced to a fluid source to inhibit corrosion of a metal containment in contact with the fluid source. One of ordinary skill in the art is able to calculate the amount of ASA-derived polyesters or composition comprising ASA-derived polyesters for a given situation without undue experimentation. Factors that would be considered important in such calculations include, for example, content of fluid source, content of corrodents, percentage water cut, and similar parameters.

In some embodiments, the ASA-derived polyesters provide from about 20-99%, 30-90%, 40-90%, 50-99%, 75-99%, 60-70%, or 75-50% corrosion inhibition for containment in contact with a fluid source. In some embodiments, the ASA-derived polyesters provide from about 50-99% corrosion protection for a containment in contact with a fluid source, as determined by a 1018 carbon steel coupon in a bubble test as described in Example 2. In some embodiments, the method provides at least 60% corrosion protection for a 1018 carbon steel coupon in a bubble test, from about 60-90%, 75-85%, 60-70%, or 80-90% wherein the bubble test is characterized by a testing temperature of about 80° C.; a $CO_2$ saturated liquid medium of 100% brine; a test duration of 2-3 hours; and a corrosion inhibitor dosage of 10 ppm, 20 ppm, 50 ppm, 75 ppm, 100 ppm, 200 ppm, 300 ppm, 400 ppm, 500 ppm, 1,000 ppm, 5,000, 7,500 ppm, or 15,000 ppm based on total fluids.

In some embodiments, the method provides at least 60% protection, from about 60-80%, 60-70%, 70-90%, 75-85% or 80-90% after two hours, at least 85% protection after 8 hours, and about 100% protection after 10 hours.

In some embodiments, the ASA-derived polyesters are more effective, on a weight basis, at inhibiting corrosion than known quaternary or imidazoline chemistries. In some embodiments, the ASA-derived polyesters inhibit corrosion of the metal surface more effectively than a conventional imidazoline corrosion inhibitors (e.g., TOFA:DETA imidazoline) or quaternary corrosion inhibitors (e.g., dimethyl benzyl ammonium chloride).

In some embodiments the ASA-derived polyesters are introduced into a fluid source by any means suitable for ensuring dispersal of the ASA-derived polyesters through the fluid source being treated. The composition comprising the ASA-derived polyesters can be injected as prepared or formulated in one or more additional solvents, depending upon the application and requirements. One of skill in the art will understand that the methods disclosed herein are not limited in any way by the introduction method, the timing or the location of the introduction.

In some embodiments, the ASA-derived polyesters are introduced to a fluid using various well-known methods and they may be introduced at numerous, different locations throughout a given system. In one embodiment, the composition comprising the ASA-derived polyester chemistry is pumped into an oil/gas pipeline using an umbilical line. In some embodiments, capillary string injection systems may be utilized to deliver the composition. U.S. Pat. No. 7,311,144 provides a description of an apparatus and methods relating to capillary injection, the disclosure of which is incorporated into the present application in its entirety. In other embodiments, the composition comprising the one or more ASA-derived polyesters are injected using mechanical equipment such as chemical injection pumps, piping tees, injection fittings, and the like.

Introducing may be achieved also by mixing, blending with mechanical mixing equipment or devices, stationary mixing setup or equipment, magnetic mixing or other suitable methods, other equipment and means known to one skilled in the art and combinations thereof to provide adequate contact and/or dispersion of the composition into the fluid source. The contacting can be made in-line and/or offline. The various components of the composition may be mixed prior to and/or during contact.

EXAMPLES

The following examples are intended to illustrate different aspects and embodiments of the specification and are not to be considered limiting the scope of the specification. It will be recognized that various modifications and changes may be made to the experimental embodiments described herein and without departing from the scope of the claims.

Example 1: Synthesis of ASA-Derived Polyester Corrosion Compound

The various corrosion inhibitor chemistries were prepared by reacting N,N,N',N'-tetrakis(2-hydroxyethyl)ethylenediamine or an ethoxylated triethylenetetramine (TETA) (commercially available from Huntsman as surfactant 2147) with an alkenyl succinic anhydride (ASA) as shown in Table 1 and described below.

TABLE 1

| Sample ID | ASA (R group) | Polyol |
|---|---|---|
| CI-1 | C16 | N,N,N',N'-tetrakis(2-hydroxyethyl)ethylenediamine |
| CI-2 | C22 | N,N,N',N'-tetrakis(2-hydroxyethyl)ethylenediamine |
| CI-3 | C16 | Surfactant 2147 |
| CI-4 | C22 | Surfactant 2147 |

Synthesis of C1-1

To a 250 mL four-necked round-bottom flask equipped with a temperature probe, nitrogen inlet, Dean-Stark apparatus, condenser, and magnetic stir bar was added heavy aromatic naphtha (20 g) and C16-ASA (42 g). N,N,N',N'-tetrakis(2-hydroxyethyl)ethylenediamine (10 g) was then charged to the stirred reaction mixture. Next, p-toluenesulfonic acid (0.1 g) was added as catalyst. The resulting mixture was heated at about 180° C. under a nitrogen blanket and stirred for about 6-8 hours or until completion of the reaction.

Synthesis of CI-2

To a 250 mL four-necked round-bottom flask equipped with a temperature probe, nitrogen inlet, Dean-Stark apparatus, condenser, and magnetic stir bar was added heavy aromatic naphtha (20 g) and C20-C24 ASA (50 g). N,N,N',N'-tetrakis(2-hydroxyethyl)ethylenediamine (8 g) was then charged to the stirred reaction mixture. Next, p-toluenesulfonic acid (0.1 g) was added as catalyst. The resulting mixture was heated to about 180° C. under a nitrogen blanket and stirred for about 6-8 hours or until completion of the reaction.

Synthesis of CI-3

To a 500 mL four-necked round-bottom flask equipped with a temperature probe, nitrogen inlet, Dean-Stark apparatus, condenser, and magnetic stir bar was added 75% aqueous solution of surfactant 2147 (40 g). The reaction flask was heated to about 140° C. under a nitrogen blanket to remove water. Next, heavy aromatic naphtha (40 g) and C16 ASA (75 g) were charged to the stirred reaction mixture. The resulting mixture was heated to about 180° C. under a nitrogen blanket and stirred for about 6-8 hours or until completion of the reaction.

Synthesis of CI-4

To a 500 mL four-necked round-bottom flask equipped with a temperature probe, nitrogen inlet, Dean-Stark apparatus, condenser, and magnetic stir bar was added 75% aqueous solution of surfactant 2147 (50 g). The reaction flask was heated to about 140° C. under a nitrogen blanket to remove water. Next, heavy aromatic naphtha (40 g) and C20-C24 ASA (60 g) were charged to the stirred reaction mixture. The resulting mixture was heated to about 180° C. under a nitrogen blanket and stirred for about 6-8 hours or until completion of the reaction.

Example 2: Corrosion Testing

The bubble cell test was used to investigate the effectiveness of the ASA-derived polyester chemistries as corrosion inhibitors. This test measures the corrosion rate of a steel electrode by aqueous linear polarization resistance (LPR). The steel electrodes (C1018) were placed in a bath of brine which was deaerated with carbon dioxide. The corrosion rate of the electrode was compared in the absence or presence of the ASA-derived polyester compounds.

The brine contained about 3 wt % of sodium chloride. The brine was placed into bubble cells and purged with $CO_2$. The brine was continually purged with $CO_2$ to saturate the brine prior to starting the test. The test cells were blanketed with $CO_2$ throughout the duration of the test to maintain saturation. The bubble cells were stirred at 100 revolutions per minute (rpm) for the duration of the test to maintain thermal equilibrium at 80° C.

After 2-3 hours of pre-corrosion time (viz., with no corrosion inhibitor or ASA-derived polyester chemistry) 20 ppm of a 10% active polyamine-polyester chemistry with 1% 2-mercaptoethanol in solvent blend was added. This equates to 2 ppm of the active chemistry with 0.2 ppm 2-mercaptoethanol being introduced into the test cell.

Comparison with known quaternary chemistry and imidazoline chemistry was made. A lower concentration (e.g., 20 ppm) was used to differentiate between the ASA-derived polyester chemistries at the same active dose. The percent inhibition was determined by comparing the inhibited corrosion rate at about 13 hours after chemical injection was made to the corrosion rate in the same test before injection was made after about 3.5 hours pre-corrosion.

Table 2 shows a corrosion rate after 13 hours after the corrosion inhibitor was injected into the test.

TABLE 2

| Candidate Chemistry | 2-Mercaptoethanol Activity (%) | Candidate Chemistry Activity (%) | Dosage (ppm) | Corrosion Rate After 13 h of CI Injection (mpy) | % Protection |
|---|---|---|---|---|---|
| | N/A | N/A | 0 | 486 | N/A |
| TOFA:DETA imidazoline salted with acetic acid | 1 | 10 | 20 | 441 | 9 |
| dimethyl benzyl ammonium chloride | 1 | 10 | 20 | 353 | 27 |
| CI-1 | 1 | 10 | 20 | 165 | 66 |
| CI-2 | 1 | 10 | 20 | 181 | 63 |
| CI-3 | 1 | 10 | 20 | 147 | 70 |
| CI-4 | 1 | 10 | 20 | 195 | 60 |

All of the ASA-derived polyester chemistries (CI-1 to CI-4) significantly outperformed that of the comparative samples (dimethyl benzyl ammonium chloride or imidazoline).

What is claimed is:

1. A composition comprising a succinic anhydride-derived polyester compound to inhibit corrosion, the succinic anhydride-derived polyester compound comprising a polyamine and an alkyl or alkenyl succinic anhydride (ASA) and having the general formula I:

(Formula I)

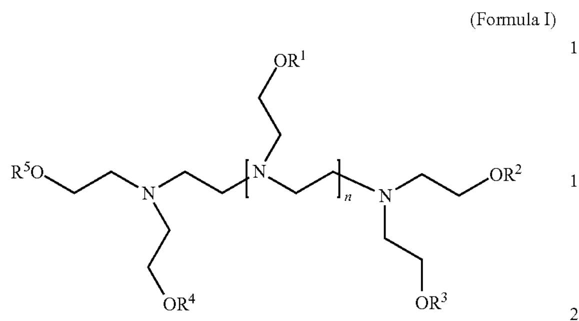

wherein n is 0-20; and wherein $R^1$, $R^2$, $R^3$, $R^4$, and $R^5$ are each individually selected from the group consisting of —H, a ring opened ASA, and a cyclic adduct with ASA, wherein at least one of $R^1$, $R^2$, $R^3$, $R^4$, and $R^5$ is an ASA or cyclic adduct with ASA or combination thereof.

2. The composition of claim 1, having a ratio of a polyamine to alkyl or alkenyl succinic anhydride in the range of about 1:1 to about 1:6.

3. The composition of claim 1, wherein n=0-2.

4. The composition of claim 1, wherein n is 0, 1 or 2, and any two, three, four, or all of $R^1$, $R^2$, $R^3$, $R^4$ and $R^5$ are ASA.

5. The composition of claim 1, wherein n=0 and any two or three of $R^1$, $R^2$, $R^3$, $R^4$ and $R^5$ are the cyclic adduct.

6. The composition of claim 1, wherein the alkyl or alkenyl group of the ASA has 5 to 25 carbon atoms.

7. The composition of claim 1 wherein the polyamine is a hydroxy-containing polyamine or an alkoxylated polyamine, wherein the polyamine optionally comprises ethoxylated diethyletriamine (DETA), ethoxylated tetraethylenpentamine (TEPA), ethoxylated pentaethylenehexamine (PEHA), N,N,N',N'-tetrakis(2-hydroxypropyl)ethylenediamine, and N,N,N',N'-tetrakis(2-hydroxyethyl)ethylenediamine, or ethoxylated triethylenetetramine (TETA).

8. The composition of claim 1, wherein the succinic anhydride-derived polyester compound is selected from the following:

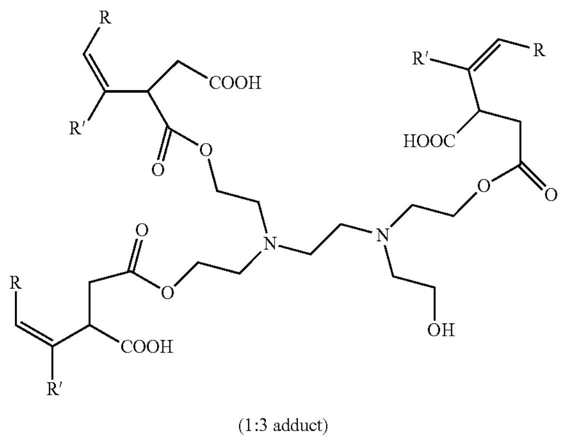

(1:3 adduct)

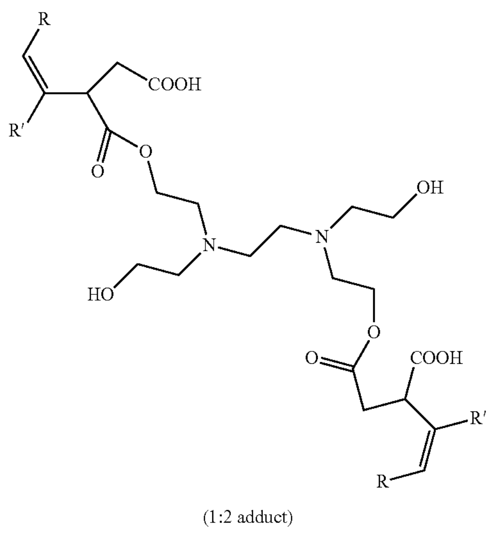

(1:2 adduct)

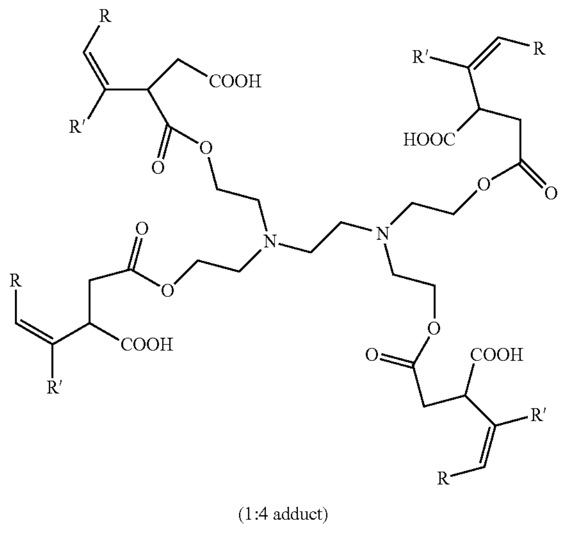

(1:4 adduct)

-continued
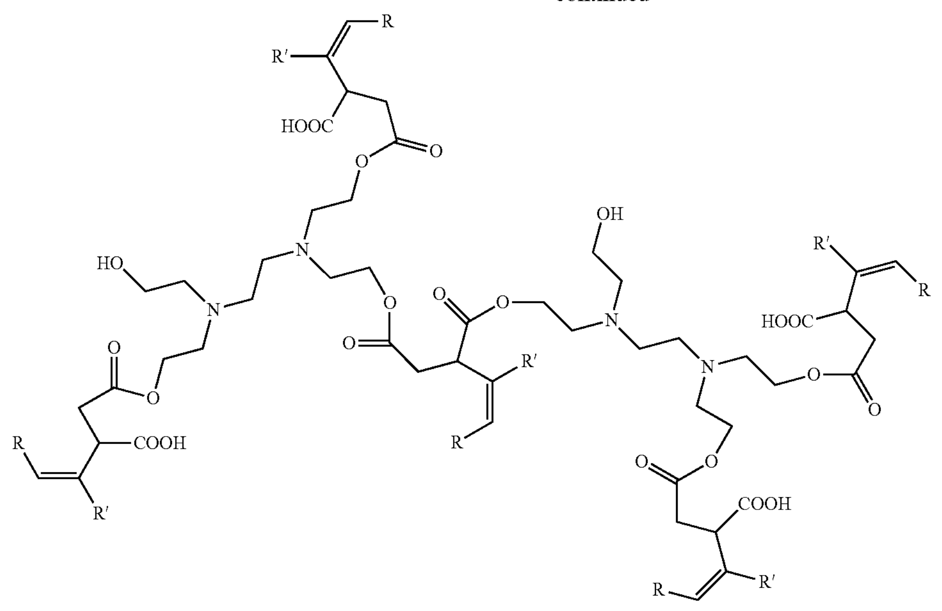
(2:5 adduct)
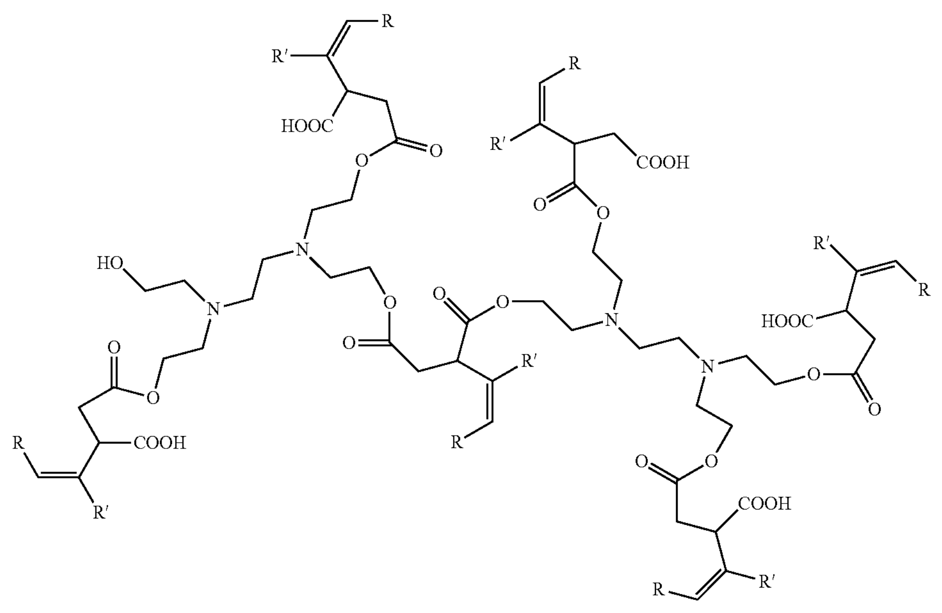
(2:6 adduct)

-continued
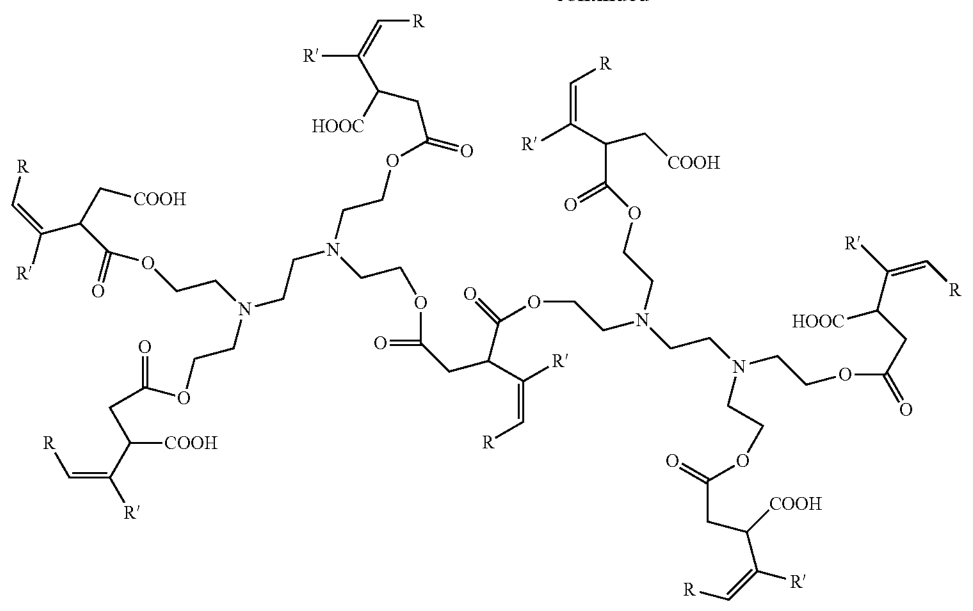
(2:7 adduct)
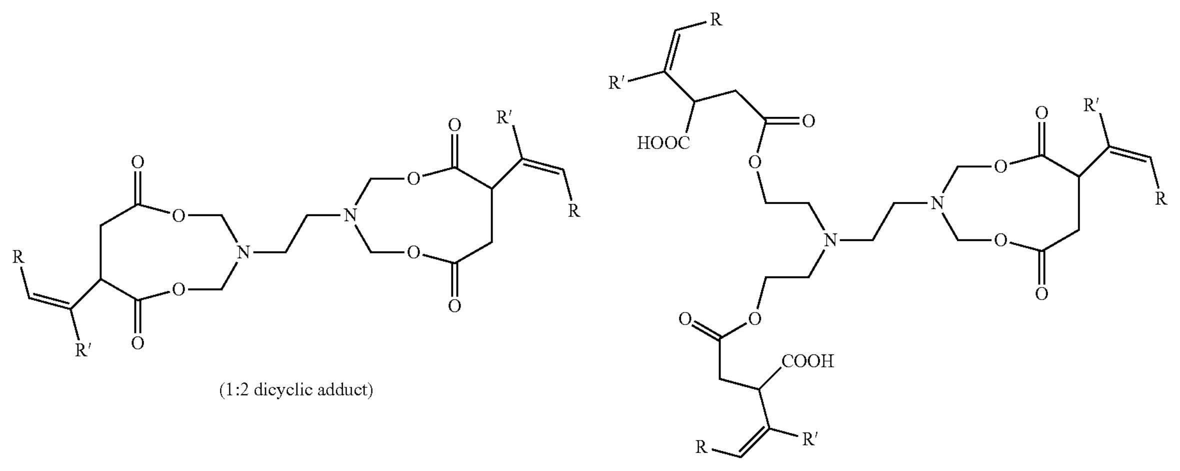
(1:2 dicyclic adduct)
(1:3 cyclic adduct)
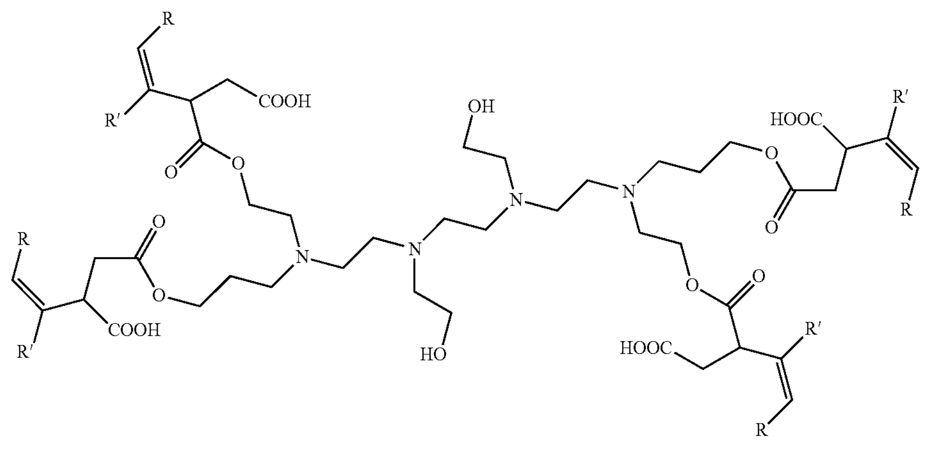
(1:4 adduct)

-continued

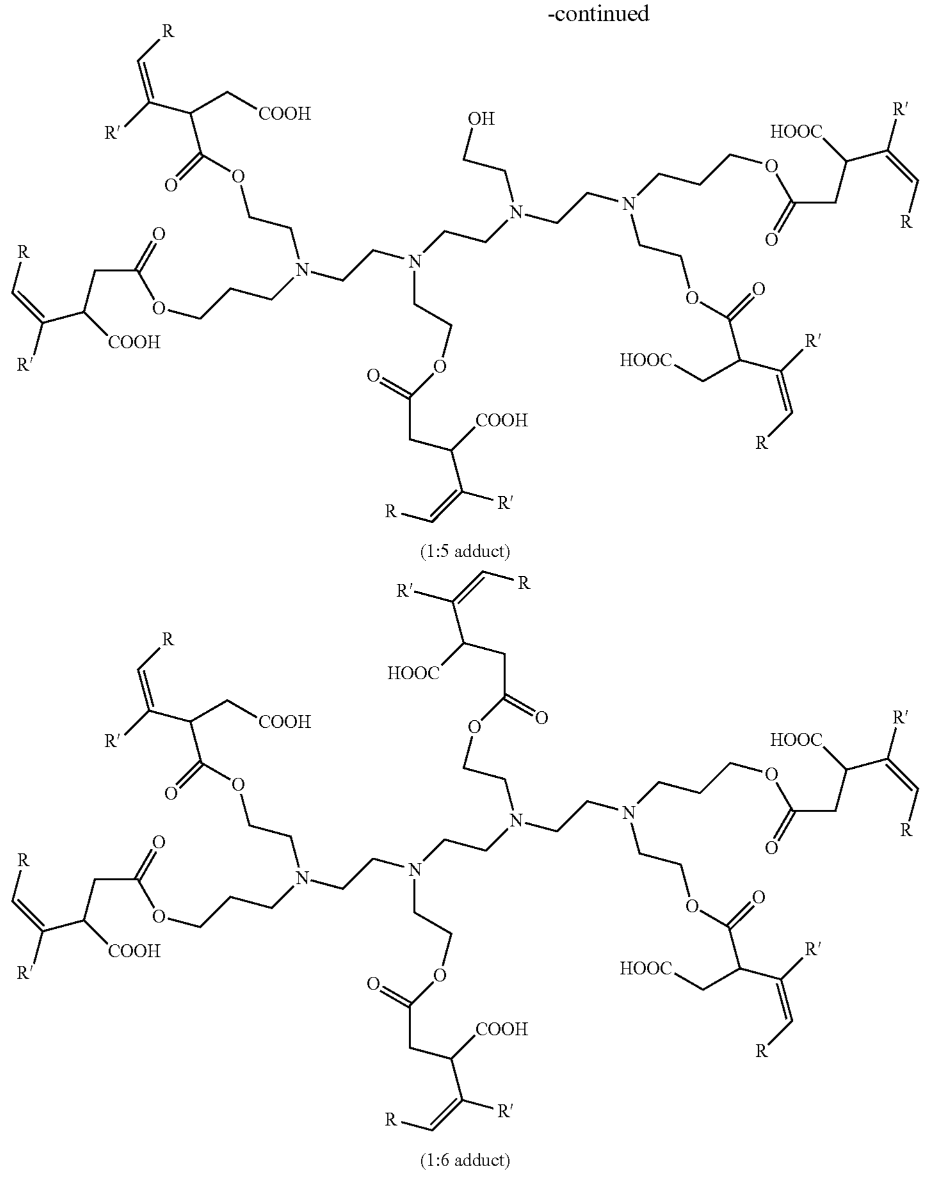

(1:5 adduct)

(1:6 adduct)

wherein R and R' are independently selected from hydrocarbon groups.

9. The composition of claim 8, wherein R and R' are independently selected from aliphatic groups, wherein optionally R and R' have a total number of carbon atoms in the range of 2-30 carbon atoms, 5-25 carbon atoms, 12-25 carbon atoms, or 16-22 carbon atoms, wherein optionally R has a number of carbon atoms in the range of 1-12, 2-11, 3-10, 4-9, or 5-8, wherein optionally R' has a number of carbon atoms in the range of 1-14, 2-13, 3-12, 4-11, or 5-10.

10. The composition of claim 1, wherein the succinic anhydride is a succinimide.

11. The composition of claim 1, wherein the succinic anhydride-derived polyester compound has a weight average molecular weight in the range of about 500 g/mol to about 10,000 g/mol.

12. The composition claim 1, further comprising an asphaltene inhibitor, a paraffin inhibitor, a scale inhibitor, a demulsifier, a water clarifier, a dispersant, an emulsion breaker, an antifoam, a salt, or combinations thereof.

13. The composition of claim 1, wherein the succinic anhydride-derived polyester is present in an amount in the range of 0.1 ppm to 10,000 ppm.

14. A composition comprising:

a fluid; and the succinic anhydride-derived polyester of claim 1, the fluid optionally comprising water, natural gas, liquid hydrocarbon, or combinations thereof.

15. A treated metal containment comprising:

a metal containment comprising a metal surface; and the fluid source comprising the succinic acid-derived polyester of claim 1, wherein the metal containment optionally comprises a tank or pipe.

16. A method of inhibiting corrosion comprising:

introducing into a process equipment or a fluid in contact with the process equipment the composition of claim 1.

17. The method of claim 16, wherein introducing is by injecting, spraying, or dripping the composition, optionally wherein introducing is carried out after or during a cleaning or during a warm up of start-up process, optionally wherein introducing is carried out intermittently, or optionally wherein introducing is carried out continuously.

18. The method of claim 16, wherein the succinic anhydride-derived polyester compound provides at least 60% inhibition of corrosion, optionally providing at least 60% corrosion protection for a 1018 carbon steel coupon in a bubble test.

19. The method of claim 16, wherein the fluid is in contact in with coils, heat exchangers, transfer line exchangers quench coolers, furnaces, separation columns or fractionators.

* * * * *